United States Patent [19]

Witucki et al.

[11] 4,440,687

[45] Apr. 3, 1984

[54] AZIDO NITRAMINO ETHERS

[75] Inventors: Edward F. Witucki, Van Nuys; Joseph E. Flanagan, Woodland Hills, both of Calif.

[73] Assignee: The United States of America as represented by the Secretary of the Air Force, Washington, D.C.

[21] Appl. No.: 366,745

[22] Filed: Apr. 8, 1982

[51] Int. Cl.$^3$ ............................................. C07C 117/00
[52] U.S. Cl. .................................... 260/349; 149/19.1
[58] Field of Search ......................................... 260/349

[56] References Cited

U.S. PATENT DOCUMENTS

| | | | |
|---|---|---|---|
| 3,122,570 | 2/1964 | Stansbury et al. | 260/349 |
| 3,873,579 | 3/1975 | Rosher | 260/349 |
| 3,883,377 | 5/1975 | Wright | 149/88 |
| 4,085,123 | 4/1978 | Flanagan et al. | 260/349 |
| 4,141,910 | 2/1979 | Flanagan et al. | 260/349 |

*Primary Examiner*—Joseph Paul Brust
*Attorney, Agent, or Firm*—Donald J. Singer; William J. O'Brien

[57] ABSTRACT

This invention involves the synthesis of a novel family of azido nitramino ethers and their utilization as energetic plasticizers for advanced solid propellant compositions. They include the novel compounds bis (2-azidoethoxymethyl) nitramine and 1,12-diazido-3,10-dioxa-5,8-dinitrazadodecane.

2 Claims, No Drawings

AZIDO NITRAMINO ETHERS

STATEMENT OF GOVERNMENT INTEREST

The invention described herein may be manufactured and used by or for the Government for governmental purposes without the payment of any royalty thereon.

BACKGROUND OF THE INVENTION

This invention relates to solid propellant compositions and to a novel family of plasticizers for use therewith. In a more specific aspect, this invention concerns itself with the use of a novel family of azido nitramino ethers as energetic plasticizers for advanced solid propellant compositions. In still another specific aspect, this invention concerns itself with the use of azido nitramino ethers as a means of reducing or minimizing the amount of flame in the exhaust gases generated during the propulsion phase of solid propellants.

The increased utilization of propellant compositions has spawned a considerable research effort in an attempt to improve their performance characteristics. Generally, solid propellants consist of one or more organic or inorganic oxidizers dispersed in a resinous binder matrix which may also function as a fuel. Typical oxidizers are ammonium perchlorate or HMX (cyclotetramethylene tetranitramine), both of which are well known in the art. Various resinous components, such as hydrocarbons, polyesters, polyurethanes and other like materials serve as the binder/fuel matrix. A supplemental fuel component, such as finely powered aluminum, may be used also. Other additive components, such as anti-oxidants, burning rate modifiers, wetting agents, anti-foaming agents and plasticizers may be added to the propellant composition, if desired. Dibutylphthalate or triacetin are generally employed as inert plasticizers in combination with the resinous binder material.

In using solid propellants, however, a problem exists in that an undesirable amount of flame is often produced in the exhaust gases during their operational phase. Excessive amounts of flame are extremely undesirable in the exhaust gases since this provides data which pinpoints the sites from which propellant operated guns, missiles or rockets are being fired. As a consequence, a continuing research effort has been maintained in an attempt to provide solid propellants with a minimum amount of flame in their exhaust gases. In furthering the research effort referred to above, it was unexpectedly discovered that a new family of azido nitramino ethers could be employed as energetic plasticizers in the fabrication of solid propellants. These novel plasticizers replace the conventional inert plasticizers generally utilized in conventional composite propellants. The resulting propellants produce a minimum amount of flame during operation.

SUMMARY OF THE INVENTION

In accordance with this invention, there is provided a novel family of azido nitramino ethers which are energetic liquids and find particular utility as energetic plasticizers in advanced solid propellants. These include bis (2-azidoethoxymethyl) nitramine (MNDA) and 1,12-diazido-3,10-dioxa-5,8-dinitrazadodecane (DDDD). They represent two examples of this family of amines and have been found to be unexpectedly effective in overcoming the problem of flame in the exhaust gases produced during the operational phase of a solid propellant composition. The energetic plasticizers of this invention, which replace the conventional inert plasticizers, are used in the propellant in a ratio of from about 1.5 to 4.0 parts of plasticizer to about 1.0 part of binder.

Accordingly, the primary object of this invention is to provide a novel family of azido nitramino ethers.

Another object of this invention is to provide a novel solid propellant composition that produces only minimum amounts of flame during its operational phase.

Still another object of this invention is to provide a novel family of azido nitramino ethers that find particular utility as energetic plasticizers for advanced solid proepllant compositions.

The above and still other objects and advantages of the present invention will become more readily apparent upon consideration of the following detailed description thereof.

DESCRIPTION OF THE PREFERRED EMBODIMENTS

With the above-mentioned and other objects in mind, the present invention contemplates the synthesis of a novel family of azido nitramino ethers and their utilization as energetic plasticizers in a conventional solid composite propellant. This novel family of amines includes bis (2-azidoethoxymethyl) nitramine (MNDA) and 1,12-diazido-3,10-dioxa-5,8-dinitrazododecane (DDDD). Both MNDA and DDDD possess physical properties that make them suitable for plasticizer use and are considerably more attractive than a conventional plasticizer such as triacetin, dibutylphthalate or (2,2,2-fluorodinitroethyl) formal (FEFO).

The synthesis of bis (2-azidoethoxymethyl) nitramine (MNDA) is illustrated by the following reaction scheme:

$$[ClCH_2CH_2OCH_2]_2NNO_2 + 2NaN_3 \rightarrow [N_3CH_2CH_2OCH_2]_2NNO_2 \quad (I)$$

Example 1 discloses the experimental details of the reaction illustrated by equation (I).

EXAMPLE 1

Bis(2-azidoethoxymethyl) nitramine (MNDA)

A mixture of 2.5 g (0.01 mole) of bis(2-chloroethoxy methyl) nitramine, 2.13 g (0.33 mole) of NaN$_3$, and 25 ml of DMF was heated at 80° C. for 1½ days. After cooling most of the DMF was removed in vacuo. Methylene chloride was added and the insoluble solid was removed via centrifugation. The methylene chloride solution was then washed 4 times with water to remove the remaining DMF. Removal of methylene chloride yielded 2.5 g (95% yield) of crude MNDA. Pure MNDA was obtained via liquid chromatography using silica gel as the adsorbent. Its structure was confirmed by ir, gc, and elemental analyzses.

| Elemental Analyses | C | H | N |
| --- | --- | --- | --- |
| Calculated for C$_6$H$_{12}$N$_8$O$_{14}$ (%) | 27.69 | 4.65 | 43.06 |
| Found (%) | 27.80 | 4.85 | 43.18 |

The snythesis of 1,12-diazido-3,10-dioxa-5,8-dinitrazadodecane (DDDD) is illustrated by equations (II a and b). It is more specifically described in Example 2:

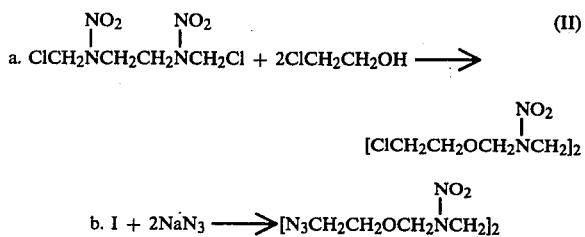

EXAMPLE 2

1,12-diazido-3,10-dioxa-5,8-dinitrazadodecane (DDDD)

A mixture of 2 g (0.006 mole) of 1,12-dichloro-3,10-dioxa-5,8-dinitrazadodecane, 1.16 g (0.018 mole) of NaN$_3$ and 25 ml of DMF was heated at 85° C. for 24 hours. After cooling the insoluble solid was removed by filtration. Methylene chloride was added and DMF was removed by washing with water. Removal of methylene chloride yielded 1.8 g (87 yield) of crude DDDD. Pure DDDD was obtained via liquid chromatography using silica gel as the adsorbent. Its structure was confirmed by ir, gc, and elemental analyses.

| Elemental Analyses | C | H | N |
| --- | --- | --- | --- |
| Calculated for $C_8H_{16}N_{10}O_6$ (%) | 27.59 | 4.63 | 40.22 |
| Found (%) | 26.70 | 4.65 | 39.91 |

The preparation of the 1,12-dichloro-3,10-dioxa-5,8-dinitrazadodecane (DCDNED) reaction component of Example 2 is illustrated by Example 3 as follows:

EXAMPLE 3

1,12-dichloro-3,10-dioxa-5,8-dinitrazadodecane (DCDNED)

A mixture of 10 g (0.04 mole) of 1,6-dichloro-2,5-dinitrazahexane, 6.8 g (0.085 mole) of 2-chloroethanol, and 50 ml of 1,2-dichloroethane was heated at 80° C. for 3 days. After cooling the solvent was removed yielding 12.2 g (90% yield) of crude DCDNED. Pure DCDNED was obtained via liquid chromatography using silica gel as the adsorbent. Its structure was confined by ir, gc, and elemental analysis.

| Elemental Analyses | C | H | N |
| --- | --- | --- | --- |
| Calculated for $C_8H_{16}N_4O_6Cl_2$ (%) | 28.66 | 4.81 | 16.71 |
| Found (%) | 28.35 | 5.50 | 16.80 |

An illustration showin the use of the novel energetic liquid plasticizers of this invention in a solid propellant composition is shown in Table I. Although an HMX oxidizer and a polyester resin binder are preferred, other conventional oxidizing and resinous binders may be utilized, if desired, as well as other fuel components, such as powdered aluminum.

Solid propellant compositions are well known and since the basic preparation and constituent ingredients of the propellant compositions of this invention are not significantly altered or critical to the execution of the invention, with the exception of the energetic plasticizer component, a detailed explanation of the propellants preparation is not deemed necessary. The plasticizers of this invention are liquid in nature and are incorporated into the solid propellant mix in a conventional manner at any stage of processing prior to cure. Generally, however, it is incorporated into the propellant mix before all the solid ingredients have been added. The resulting solid propellant differs from a conventional composition only in the essential replacement of the typical inert plasticizer with the novel energetic plasticizers of this invention.

TABLE I

| Propellant Composition (Weight %) | | |
| --- | --- | --- |
| HMX | 75 | 75 |
| Polyester resin | 10 | 10 |
| MNDA | 15 | — |
| DDDD | — | 15 |

While the present invention has been described by reference to particular embodiments thereof, it should be understood by those skilled in the art that all the modifications that are encompassed within the scope of the appended claims are intended to be included herein.

What is claimed is:

1. As a new compound, bis(2-azidoethoxymethyl) nitramine.

2. As a new compound, 1,12-diazido-3,10-dioxa-5,8-dinitrazadodecane.

* * * * *